United States Patent
Kurnik et al.

[11] Patent Number: 6,139,718
[45] Date of Patent: *Oct. 31, 2000

[54] ELECTRODE WITH IMPROVED SIGNAL TO NOISE RATIO

[75] Inventors: Ronald T. Kurnik, Foster City; Janet Tamada, Mountain View; Michael J. Tierney, San Jose, all of Calif.

[73] Assignee: Cygnus, Inc., Redwood City, Calif.

[*] Notice: This patent issued on a continued prosecution application filed under 37 CFR 1.53(d), and is subject to the twenty year patent term provisions of 35 U.S.C. 154(a)(2).

[21] Appl. No.: 08/824,143

[22] Filed: Mar. 25, 1997

[51] Int. Cl.$^7$ ..................................................... G01N 27/26
[52] U.S. Cl. ......................... 205/777.5; 205/792; 204/403
[58] Field of Search ..................... 204/703, 289, 204/550, 412, 280; 205/777.5, 792; 600/346, 365, 347, 345, 353, 357

[56] References Cited

U.S. PATENT DOCUMENTS

| | | |
|---|---|---|
| 3,954,925 | 5/1976 | Böddcker . |
| 4,073,713 | 2/1978 | Newman . |
| 4,388,166 | 6/1983 | Suzuki et al. . |
| 4,571,292 | 2/1986 | Liu et al. ............................... 204/412 |
| 5,279,543 | 1/1994 | Glikfeld et al. . |
| 5,362,307 | 11/1994 | Guy et al. ................................. 604/20 |
| 5,562,307 | 10/1996 | Connor . |
| 5,730,714 | 3/1998 | Guy et al. ................................. 604/20 |
| 5,735,273 | 4/1998 | Kurnik et al. ........................... 128/635 |
| 5,741,634 | 4/1998 | Nozoe et al. ............................... 435/4 |
| 5,766,934 | 6/1998 | Guiseppi-Elie ....................... 435/287.9 |
| 5,771,890 | 6/1998 | Tamada ................................... 128/635 |
| 5,827,183 | 10/1998 | Kurnik et al. ........................... 600/345 |

FOREIGN PATENT DOCUMENTS

| | | |
|---|---|---|
| 62-133937 | 6/1987 | Japan . |
| WO 96/00109 | 1/1996 | WIPO . |
| WO 96/00110 | 1/1996 | WIPO . |
| WO 97/02811 | 1/1997 | WIPO . |
| WO 97/24059 | 7/1997 | WIPO . |

OTHER PUBLICATIONS

Petek, M., et al., (1971) "Spectroelectrochemistry–Application of Optically Transparent Minigrid Electrodes under Semi–Infinite Diffusion Conditions," *Anal. Chem.* 43(8): 1069–1074.

Pons, S., et al., (1987) "The Behavior of Microelectrodes," *Anal. Chem.* 59(24): 1391A–1399A.

*Primary Examiner*—T. Tung
*Assistant Examiner*—Alex Noguerola
*Attorney, Agent, or Firm*—Barbara G. McClung; Robins & Associates

[57] ABSTRACT

An electrode assembly for sensing an electrochemical signal diffused from a source to a working electrode which is comprised of a plurality of substantially separated working electrode surfaces is disclosed. The electrode of the invention is comprised of 1) a working electrode made up of a plurality of working electrode surfaces or components and 2) a electrically insulating gap defined by adjacent edges of 1) insulating the working electrode surfaces or components from each other. The working electrode components are configured to receive electrochemical signal from two or preferably three dimensions simultaneously. The working electrode components configured over the same surface as a single electrode provide (1) an improved signal to noise ratio as compared to a single electrode by reducing noise, and (2) provide an overall enhanced signal after sensing for a given period of time.

24 Claims, 7 Drawing Sheets

ELECTRODE WITH IMPROVED SIGNAL TO NOISE RATIO

FIELD OF THE INVENTION

The invention relates generally to the field of electrodes for electrochemical measurements, specifically electrodes used in the biomedical fields to measure concentrations of biomedically significant compounds.

BACKGROUND OF THE INVENTION

The amount of a chemical in a given volume of solution can be measured with an electrode. An electrode is the component in an electrochemical cell in contact with the electrolyte medium through which current can flow by electronic movement. Electrodes, which are essential components of both galvanic (current producing) and electrolytic (current using) cells, can be composed of a number of electrically conductive materials, e.g., lead, zinc, aluminum, copper, iron, nickel, mercury, graphite, gold, or platinum. Examples of electrodes are found in electric cells, where they are dipped in the electrolyte; in medical devices, where the electrode is used to detect electrical impulses emitted by the heart or the brain; and in semiconductor devices, where they perform one or more of the functions of emitting, collecting, or controlling the movements of electrons and ions.

The electrolyte can be any substance that provides ionic conductivity, and through which electrochemically active species can diffuse. Electrolytes can be solid, liquid, or semisolid (e.g., in the form of a gel). Common electrolytes include sulfuric acid and sodium chloride, which ionize in solution. Electrolytes used in the medical field must have a pH that is sufficiently close to that of the tissue in contact with the electrode (e.g., skin) so as not to cause harm to the tissue over time.

Electrochemically active species that are present in the electrolyte can undergo electrochemical reactions (oxidation or reduction) at the surface of the electrode. The rate at which the electrochemical reactions take place is related to the reactivity of the species, the electrode material, the electrical potential applied to the electrode, and the rate at which the electrochemically active species is transported to the electrode surface.

In unstirred electrolytes, such as quiescent liquid solutions and gel electrolytes, diffusion is the main process of transport of electrochemically active species to the electrode surface. The exact nature of the diffusion process is determined by the geometry of the electrode (e.g., planar disk, cylindrical, or spherical), and the geometry of the electrolyte (e.g., semiinfinite large volume, thin disk of gel, etc.) For example, diffusion of electrochemically active species to a spherical electrode in a semiinfinite volume of electrolyte differs from diffusion of electrochemically active species to a planar disk electrode. At the center of the disk electrode the diffusion of the electroactive species towards the electrode is in a substantially perpendicular direction, whereas at the edges of the disk electrode the diffusion comes from both perpendicular and radial directions. The combination of these two different diffusion patterns makes the total current collected at the disk electrode.

The present invention makes use of a unique geometry of the electrode surface such that the diffusion of the electrochemically active species in the radial and axial direction gives a total signal higher than if there was only diffusion in the axial direction, thus allowing the use of a decreased surface area of the electrode surface, particularly for the case of an electrolyte of finite volume.

SUMMARY OF THE INVENTION

An electrode assembly is disclosed that includes a multicomponent working electrode subassembly comprised of a plurality of substantially physically separated working electrode surfaces (e.g., a plurality of working electrode components). When surfaces of the working electrode subassembly are configured over an area that is equal to the area of a single piece working electrode, the multicomponent electrode will provide an improved signal to noise ratio due to reduced noise, and will provide an enhanced signal when measuring signal from a finite amount of medium over a finite amount of time. A working electrode of the invention provides a substantially discontinuous surface area in contact with a medium through which a compound will diffuse in response to a current. Noise created by the electrode material is reduced by reducing the surface area per individual working electrode surface, and the signal is enhanced by allowing diffusion to multiple working electrode surfaces via two and preferably three dimensions, e.g., (1) normal to the main surface plane, (2) normal to the length edge, and (3) normal to the width edge. By using a substantially discontinuous surface, a large number of edges are provided within the area being monitored. In the presence of edges, the flux for the species of interest is significantly higher (at the edge, due to radial diffusion) thus giving a higher overall flux over the area of interest that is greater than that if there was only diffusion directly perpendicular to the main surface plane of the electrode of interest.

The invention features an electrode subassembly comprised of interconnected electrode surfaces that form a working electrode, with each of the electrode components being separated from the others by an electrically insulating gap.

An object of the invention is to provide a working electrode comprised of substantially discontinuous working electrode surfaces or components and thereby obtain signal from three dimensions which provide an improved signal to noise ratio.

Another object is to provide a method for measuring an electrochemical signal by providing substantially discontinuous working electrode surfaces or components that detect the flux of the electrochemical signal in two or more preferably three directions relative to the working electrode surface.

Another object of the invention is to provide an electrode subassembly composed of a working electrode comprised of substantially discontinuous working electrode surfaces for use with an electrode assembly to measure accurately, consistently, and quickly a diffused electrochemical signal, and achieve an accurate measurement of the electrochemical signal within a matter of seconds to minutes.

Another object of the invention is to provide an electrode assembly with a bonding pad or a pad that contacts a pin connector that can be readily connected and disconnected from a power source and monitoring device, thus allowing for replacement of the electrode assembly, electrode subassembly, and/or an ionically conductive material (e.g., an electrolytic gel) used with the electrode assembly.

An advantage of the working electrode is that it provides an improved signal to noise ratio by reducing noise and allowing a signal to be produced equivalent to a solid electrode but only using one half or less of the surface area of a solid electrode.

Another advantage of the invention is that the electrode can be used to measure very low concentrations of an electrochemical signal in an electrolyte (i.e., an ionically conductive material). For example, the electrode can be used in conjunction with a hydrogel system for monitoring glucose levels in a subject (e.g., a human). An electroosmotic electrode (e.g., iontophoresis or reverse iontophoresis electrodes) can be used electrically to draw glucose into the hydrogel. Glucose oxidase (GOD) contained in the hydrogel converts the glucose into gluconic acid and hydrogen peroxide. The electrode subassembly catalyzes the hydrogen peroxide into an electrical signal. This system allows for the continuous and accurate measurement of an inflow of a very small amount of glucose in an electrolyte (e.g., glucose concentrations 10, 500, or 1,000 or more times less than the concentration of glucose in blood).

Another advantage is that the electrode assembly and electrode subassembly are easily and economically produced.

A feature of the electrode subassembly of the invention is that it is small and flat, having a total surface area in the range of about 0.1 $cm^2$ to 8.0 $cm^2$. If desired, the electrode subassembly can also be quite thin, such that it has a thickness in the range of about 0.25 μm to 250 μm.

These and other objects, advantages and features of the present invention will become apparent to those persons skilled in the art upon reading the details of the composition, components and size of the invention as set forth below, reference being made to the accompanying drawings forming a part hereof wherein like numbers refer to like components throughout.

DESCRIPTION OF THE PREFERRED EMBODIMENTS

Figure 1:
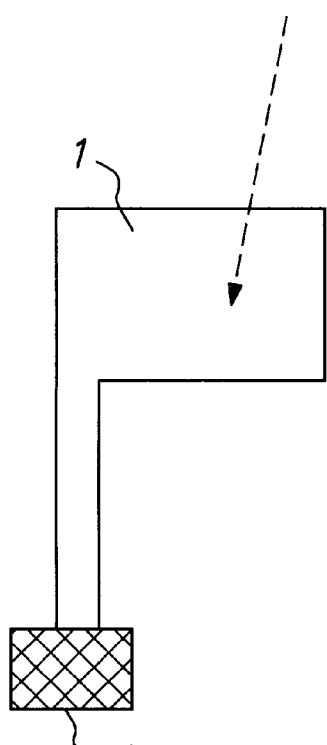
FIG. 1 is an overhead schematic view of a conventional one dimensional working electrode.

Before the electrode of the present invention is described and disclosed it is to be understood that this invention is not limited to the particular components or composition described as such may, of course, vary. It is also to be understood that the terminology used herein is for the purpose of describing particular embodiments only, and is not intended to be limiting since the scope of the present invention will be limited only by the appended claims.

It must be noted that as used in this specification and the appended claims, the singular forms "a," "an" and "the" include plural referents unless the context clearly dictates otherwise. Thus, for example, reference to "a molecule" includes a plurality of molecules and different types of molecules.

Unless defined otherwise all technical and scientific terms used herein have the same meaning as commonly understood by one of ordinary skill in the art to which this invention belongs. Although any materials or methods similar or equivalent to those described herein can be used in the practice or testing of the present invention, the preferred methods and materials are now described. All publications mentioned herein are incorporated herein by reference for the purpose of describing and disclosing the particular information for which the publication was cited in connection with. Although cited publications may be published prior to the filing date such does not mean that such publications cannot be antedated by virtue of an earlier date of invention.

Definitions

The term "electrode subassembly" means a working electrode comprised of a plurality or group of substantially discontinuous working electrode surfaces (e.g., components), where the adjacent edges of the group of working electrode surfaces define an electrically insulating gap and wherein the group of working electrode surfaces allow for multidimensional diffusion. The working electrode surfaces (e.g., components) can be configured in two or more strips to allow for two dimensional diffusion, or in two or more squares to allow for three dimensional diffusion.

The phrase "substantially discontinuous working electrode surfaces" or "substantially physically separated electrode surfaces" is meant to describe a working electrode that comprises a plurality of working electrode surfaces that are electrically connected, but otherwise substantially separated one from another (i.e., the adjacent edges of the working electrode surfaces of the working electrode are separated by an electrically insulating gap and the group of working electrode surfaces allow for multidimensional diffusion).

The term "electrode assembly" means an assembly comprised of 1) an electrode subassembly, 2) an electroosmotic electrode (e.g., iontophoresis electrode), and 3) reference and counter electrodes. The electrode assembly can additionally include a substrate (e.g., a ceramic or polymeric substrate) to which the electrode assembly and electroosmotic, reference, and counter electrodes are attached.

The term "working electrode" means one or more substantially discontinuous electrode surface(s) or components that are monitored to determine the amount of electrical signal generated at the combined surface which cover a defined area to be monitored. The amount of signal generated is correlated with the amount of a chemical compound present in an electrolyte which contains a compound which generates the electrical signal on contact with a surface of working electrode. The working electrode comprises substantially discontinuous catalytic surfaces which allow for multidimensional diffusion of compound to the catalytic surfaces. The catalytic surfaces are comprised of a material selected from the group consisting of platinum, palladium, nickel, carbon, noble metals (e.g., gold), and oxides, dioxides and alloys thereof.

The term "electrically insulating gap" means the space defined by the adjacent edges of the outer perimeter of the area defined by the working electrode. The electrically insulating gap electrically isolates the individual surfaces or components from each other by virtue of the width of the gap itself, and/or by virtue of an electrically insulating material contained within the gap.

The term "catalytic surface" or "catalytic face" are used interchangeably herein to mean the surface of the working electrode components that: 1) is in contact with the surface of an electrolyte containing material through which the chemical signal flows from a source of chemical signal; 2) is comprised of a catalytic material (e.g., platinum, palladium, or nickel and/or oxides, dioxides and alloys thereof); 3) catalyzes the conversion of the chemical signal into an electrical signal (i.e., an electrical current); and 4) defines the total working electrode surface area (all working electrode components) that, when composed of a catalytic material, is sufficient to drive the electrochemical reaction at a rate sufficient to generate a detectable, accurate electrical signal that is correlatable with the amount of chemical signal present in the electrolyte. Only that electrical signal generated at the catalytic surface of the working electrode is correlated with the amount of chemical signal present in the electrolyte.

The term "chemical signal," or "electrochemical signal," and the like are used interchangeably and mean the chemical compound that is ultimately converted to an electrical signal at the catalytic faces of the working electrode components. "Chemical signals" can be: 1) directly converted into an electrical current by chemical reaction at the catalytic faces of the electrode subassembly; or 2) indirectly converted into an electrical signal by the action of one or more catalysts. For example, the chemical signal glucose is indirectly converted into an electrical signal by reactions driven by two catalysts. A first catalyst glucose oxidase (GOD), which is present in the electrolyte containing material (e.g., a hydrogel patch), converts glucose into gluconic acid and hydrogen peroxide. Hydrogen peroxide is then converted to a measured electrical current upon electrochemical oxidation by platinum (the second catalyst) on the catalytic faces of all of the working electrode components making up the electrode subassembly. Preferably, the chemical signal is generated by catalytic action on a biomedically significant compound (e.g., glucose).

"Ionically conductive material" or "medium" means a material that provides ionic conductivity, and through which electrochemically active species can diffuse. The medium will allow diffusion in three dimensions, i.e., normal to a planar surface of a working electrode component, normal to a length edge of the working electrode component and normal to a width edge of a working electrode component. The ionically conductive material can be, for example, a solid, liquid, or semisolid (e.g., in the form of a gel) material that contains an electrolyte, which can be composed primarily of water and ions (e.g., sodium chloride), and generally comprises 50% or more water by weight. The material can be in the form of a gel, a sponge or pad (e.g., soaked with an electrolytic solution), or any other material that can contain an electrolyte and allow passage of electrochemically active species, especially the chemical signal of interest, through it.

Electrode (General)

The invention must have some basic characteristics in order to be useful for its intended purpose, which is to detect a chemical signal in a manner such that the amount of signal detected can be related to the amount of signal in a given source, e.g., detect hydrogen peroxide generated by glucose oxidase (GOD) catalysis of glucose. The electrode assembly and medium must: (1) enable ions to flow in more than one dimension toward surfaces of the electrode subassembly; (2) be easy and inexpensive to manufacture; (3) have a size such that the surface area of one face of the electrode assembly is in the range of about 0.1 $cm^2$ to 8.0 $cm^2$, and a thickness of less than 1 mm wherein all components of the electrode assembly are in substantially the same plane; and (4) include an electrode subassembly comprised of substantially discontinuous working electrode surfaces, e.g., separated working electrode components, which catalyze substantially all chemical signals which diffuse inward from the area surrounding the area defined by the electrode subassembly—all in a portable unit sufficiently small such that the unit can be worn as a watch is worn and weigh less than 0.25 kilograms.

As used herein, "surface area" means the geometric surface area (e.g., the geometric surface area of a circular electrode defined by the formula $\pi r^2$), without accounting for microscopic surface roughness that can contribute to the actual, three-dimensional surface area. The microscopic surface area is important in considering the actual, three-dimensional surface area available to, for example, drive the electrochemical conversion of the chemical signal to an electrical signal. The surface of an electrode subassembly is the sum of all of the surface areas of each component or surface of the working electrode but not including any space or gap that exists between the components or between solid areas of a substantially discontinuous single working electrode surface.

For reasons that may relate to factors such as the build up of undesired materials in the electrode assembly and/or electrode subassembly, the electrode assembly and/or electrode subassembly must be easily replaceable (e.g., by a user) in a convenient manner. In general, the electrode assembly and/or electrode subassembly is designed for use in continuous chemical signal sensing over a period ranging from about 1 day to 1 month, preferably about 1 week to 2 weeks, more preferably about 2 weeks to 4 weeks or more. After such time, the electrode is preferably designed so that it is disposable (e.g., can be readily detached from the monitoring device and replaced with a new electrode subassembly and/or electrode assembly). Accordingly, the electrode assembly must have some structural integrity, and provide for the detection of the chemical signal of interest. In that the electrode assembly and sensor housing containing the electrode assembly is preferably small (e.g., hand held, e.g., the size of a watch to be worn on the wrist of a patient and weighing about 0.25 kilograms or less). If desired, the electrode assembly and electrode subassembly can be particularly thin, e.g., in the range of 0.25 $\mu$m to 250 $\mu$m. In order to measure accurately the amount of a chemical signal (e.g., the amount of hydrogen peroxide generated by GOD catalysis of glucose) and be sufficiently large to be manipulated, the electrode assembly cannot be too thin and cannot be too small.

The overall surface area of the complete electrode assembly (which includes the electrode subassembly) on a single surface should be in the range of about 0.25 $cm^2$ to about 8 $cm^2$, preferably about 0.50 $cm^2$ to 2 $cm^2$.

Basic Structure of the Electrode Subassembly

Figure 2:
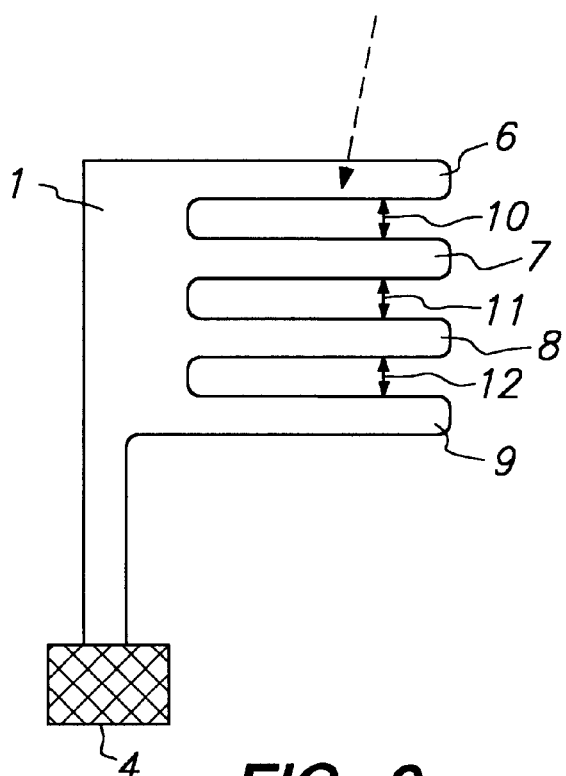
FIG. 2 is an overhead schematic view of a two dimensional working electrode.
Figure 3:
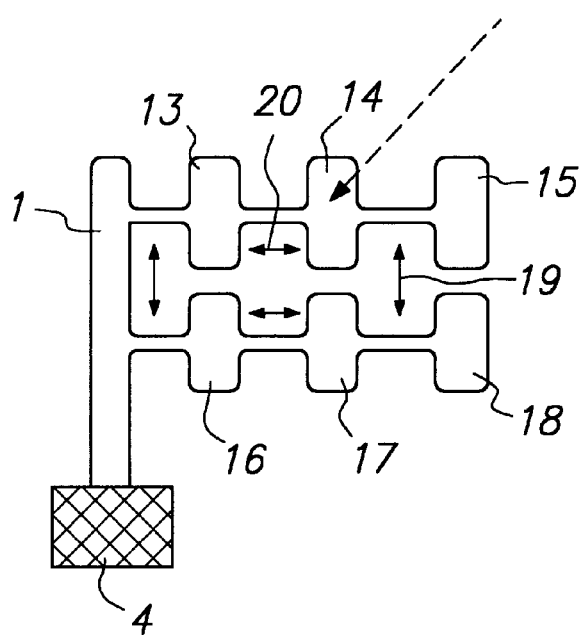
FIG. 3 is an overhead schematic view of a three dimensional working electrode.

FIGS. 1, 2, and 3 are overhead schematic views of exemplary embodiments of an electrode subassembly. The embodiments of FIGS. 1, 2 and 3 allow migration to electrode surface (2) from one, two and three dimensions respectively. FIGS. 2 and 3 show embodiments of the invention. The basic structural components of the electrode subassembly are the working electrode comprised of substantially discontinuous working electrode surfaces as per FIGS. 2 and 3. These components can be configured in a variety of ways.

Some of the basic configurations of the working electrode components are shown within FIGS. 1, 2, 3, 5, 7, 8, 9 and 10. FIG. 1 shows a basic configuration wherein the arrow leading towards the working electrode 1 is intended to represent electrochemical signal diffusing toward the surface of the working electrode 1 from a direction normal to the page on which the electrode 1 is drawn. Thus, electrochemical signal diffuses toward the surface of the working electrode 1 via a single dimension. These basic concepts are followed per the present invention. However, per the present invention, electrochemical signal can diffuse to a surface or edge of the working electrode 1 via two different and preferably three different dimensions.

As shown in FIG. 2 the working electrode 1 includes working electrode component strips 6, 7, 8 and 9, which are separated from each other by gaps 10, 11 and 12. In this "strip" configuration it is possible to detect electrochemical signal diffusing to the working electrode 1 via the path normal to the page as per FIG. 1 and signal which diffuses in a direction substantially parallel to the page (from top to bottom) as shown by the arrows within the gaps 10, 11 and 12.

A more preferred embodiment of the invention is shown within FIG. 3 wherein the electrochemical signal can diffuse toward the working electrode 1 via three different dimensions. More specifically, the working electrode 1 includes substantially separate discontinuous surface areas 13, 14, 15, 16, 17 and 18. These surface areas are separated from each other by gaps such as gaps 19 and 20. Thus, per this configuration electrochemical signal can diffuse to a surface of a working electrode component from a direction normal to the page as per FIG. 1. Further, electrochemical signal can diffuse to a surface or edge of a working electrode component via a direction parallel to the page in the top/bottom direction as per the arrow in the gap 19 which is similar to that shown in FIG. 2. Lastly, electrochemical signal can diffuse to a surface or edge of a working electrode from a direction parallel to a line drawn to the side edges of the page as per the arrow shown in the gap 20. Thus, electrochemical signal diffuses to the working electrode components 13–18 via three different dimensions: (1) normal to the planar surface; (2) normal to a length edge; and (3) normal to a width edge.

Electrodes which are used in order to sense electrochemical signals, and in particular biosensors are often compromised by the inherent background signal that is present when these sensors are used. This background signal or noise is generally due to oxidation of a metal electrode surface. Accordingly, the noise is proportional to the amount of electrode surface area. In order to reduce the noise it is possible to decrease the surface area of the electrode. However, by decreasing the surface area the signal is decreased thus the signal to noise ratio is not improved.

In each of FIGS. 1, 2, and 3 the working electrode has a surface area smaller than if this electrode were a continuous solid due to the presence of the gaps between the substantially discontinuous surface areas of the working electrode. Thus, the configuration in FIG. 2 creates less noise than that of FIG. 1, and the configuration in FIG. 3 creates less noise than that of FIG. 2. Even though the configurations of FIGS. 2 and 3 create less noise, they can actually generate an enhanced signal when the reading is taken over a defined (i.e., limited or finite) period of time as compared with the signal generated by the configuration of FIG. 1. The enhanced signal is created by receiving electrochemical signal from two or three directions as opposed to substantially only one direction as per the system of FIG. 1.

Regardless of the configuration of the working electrode 1 it is constructed and operates in essentially the same manner. Thus, before describing the particular details of the operation of particular embodiments such as those shown in FIGS. 2 and 3, a general description of the working electrode is provided.

Figure 7:
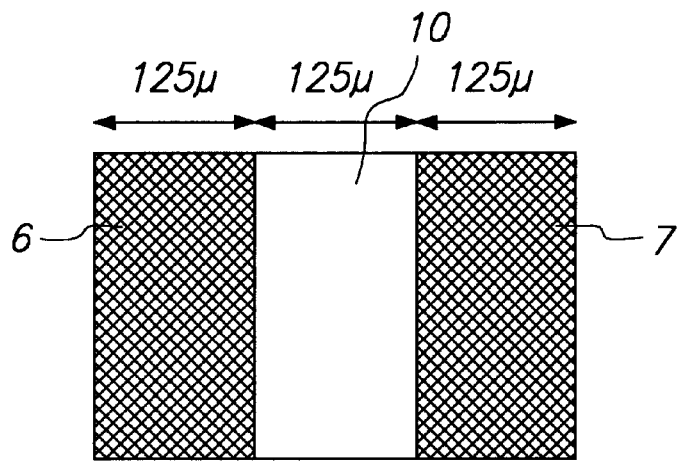
FIG. 7 is an overhead plan view of a simple "strip" embodiment of a working electrode of the invention.
Figure 8:
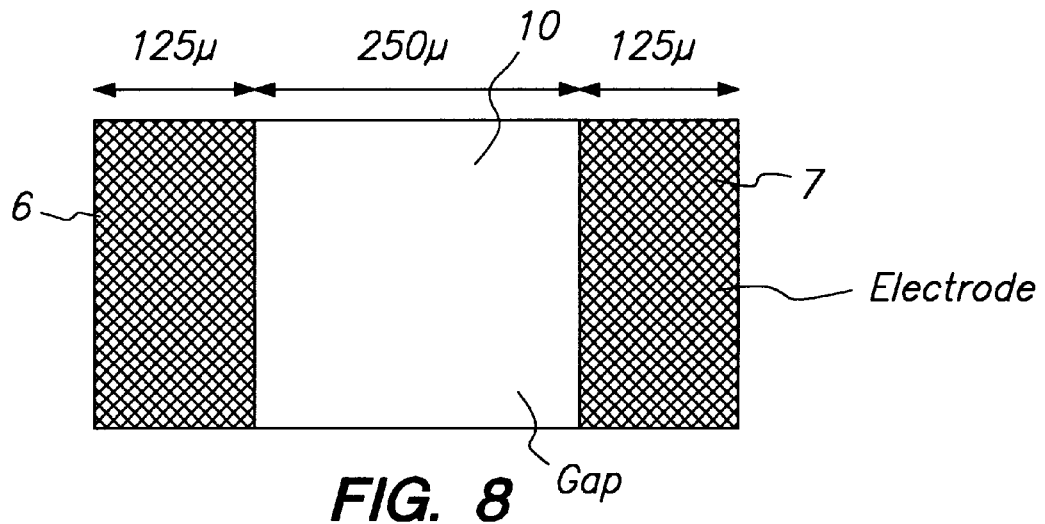
FIG. 8 is an overhead view of another simple embodiment of a "strip" configuration of a working electrode of the invention.
Figure 9:
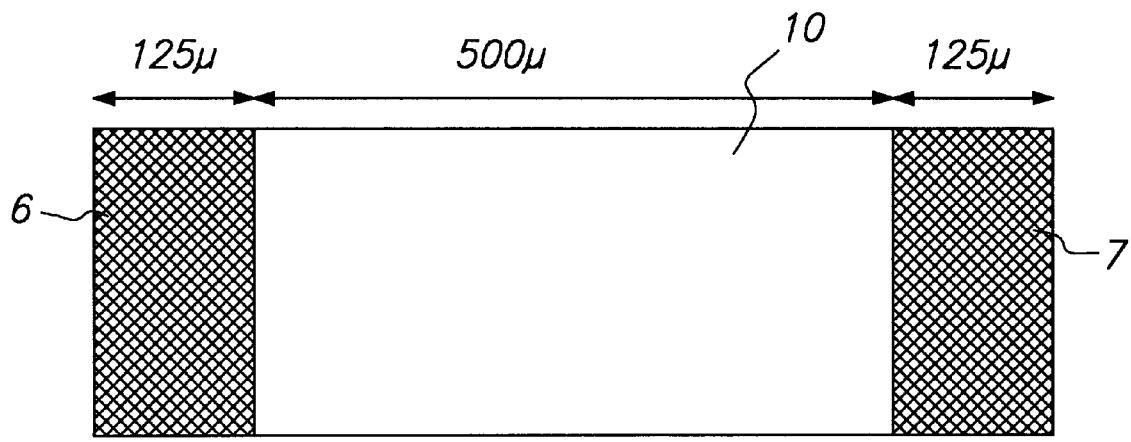
FIG. 9 is yet another embodiment of a simple "strip" embodiment of a working electrode of the invention.
Figure 11:
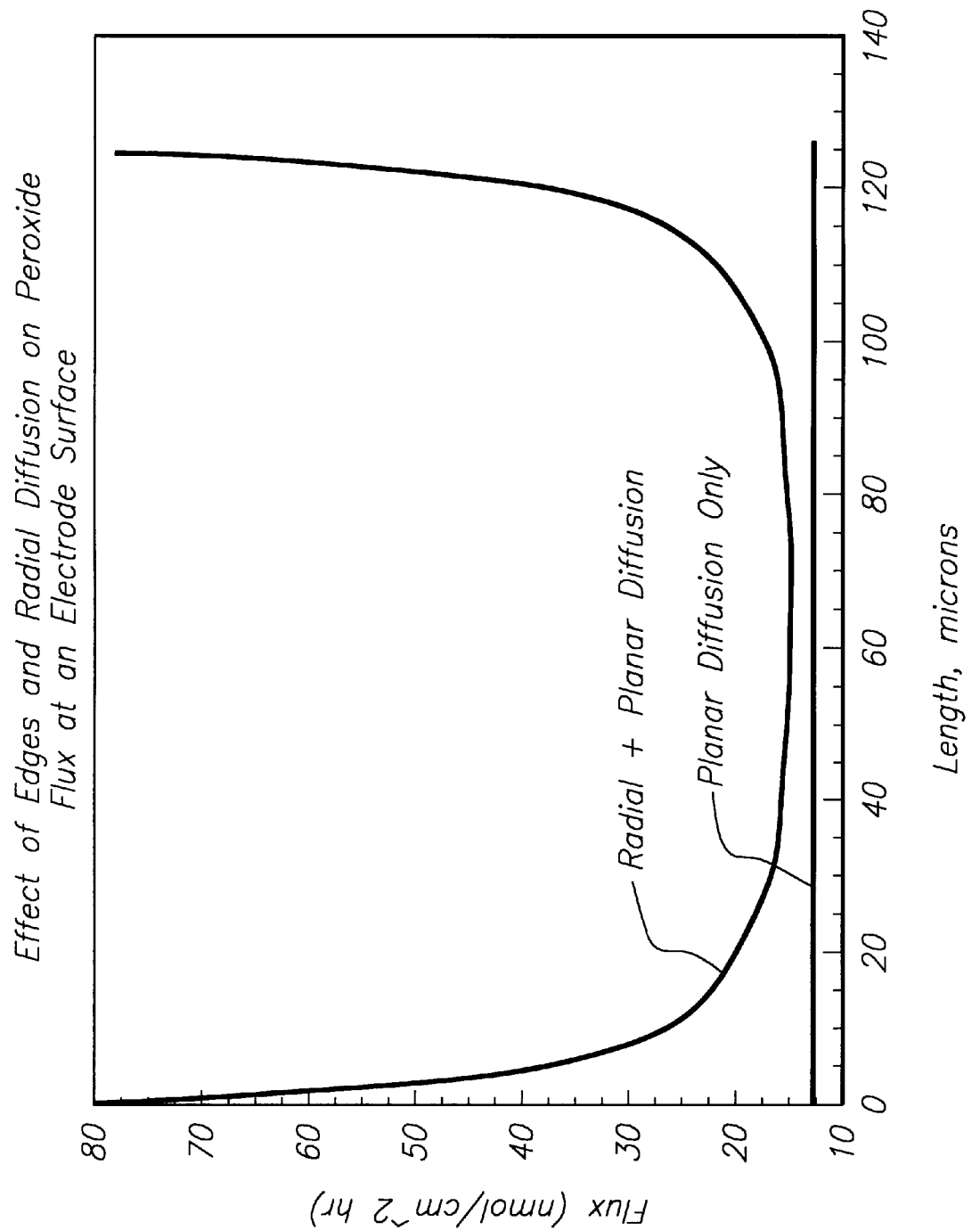
FIG. 11 is a graph comparing the embodiment of FIG. 8 with a single planar continuous working electrode surface.

The basic "strip" configuration of working electrodes of the present invention are shown within FIGS. 7, 8 and 9. The configurations differ only in that the "gap" is different for each configuration. In FIG. 7 each strip 6 and 7 has a width of 125 microns and the gap 10 has a width of 125 microns. In FIG. 8 each strip 6 and 7 has a width of 125 microns and the gap 10 has a width of 250 microns. In FIG. 9 each strip 6 and 7 has a width of 125 microns and the gap 10 has a width of 500 microns. FIG. 11 compares the flux readings obtained for a configuration as per FIG. 8 with a single piece planar working electrode. As is shown in FIG. 11 the flux is substantially increased at or near the edges.

As described above with reference to FIGS. 7, 8 and 9 (and FIGS. 1, 2 and 3), the electrode subassembly can also be configured in a variety of ways with respect to the configuration of the electrically insulating gap. The electrically insulating gap 3 can be an empty space between the working electrodes, the width of the gap serving electrically to isolate the two electrodes. Alternatively, the electrically insulating gap can contain an electrically insulating material of substantially the same thickness as the working electrodes, and separating the working electrodes. The electrically insulating material can be configured as a single piece, or can be present as several smaller pieces of material positioned at various points along the working electrodes' adjacent edges. The electrically insulating material can contact substantially the entire perimeter of the adjacent electrodes' edges, or contact only portions of one or both of the working electrode edges. Alternatively, the electrically insulating material can be an area of substrate between the two electrodes on which no electrically conductive material is coated (e.g., the ceramic substrate onto which the electrode assembly is printed can serve as the electrically insulating material).

In a preferred embodiment, the working electrode surfaces and the electrically insulating gaps are provided in a "checkerboard" configuration. An electrode subassembly that has a checkerboard configuration is one in which working electrode surfaces are provided as a plurality of square-shaped regions, with the working electrode surfaces being isolated from each other by a plurality of rectangular (e.g., square) gaps. In a checkerboard configuration, the working electrode surfaces are configured in a repeating pattern. A schematic representation of an exemplary electrode subassembly having a checkerboard configuration is provided in FIG. 10, and a variety of methods can be used to produce such a subassembly. For example, the working electrode components can be provided as a plurality of strips that are configured parallel to each other. Working electrode surfaces then are configured as a plurality of square-shaped regions by depositing strips of electrically insulating material onto the strips of working electrodes, and at 90° angles relative to the strips of working electrodes. Those skilled in the art will recognize that, as is described above for the construction of an electrode subassembly in general, alternate methods can be used to produce an electrode subassembly having a checkerboard configuration. For example, several small pieces of electrically insulating material can be used to produce the checkerboard, or a single piece of electrically insulating material having square holes can be placed over a working electrode component(s). When present in a checkerboard configuration, the working electrode surfaces preferably each are configured as squares having a width of about 125 $\mu$m.

In general, the width of the electrically insulating gap (and/or the width and location of the electrically insulating material contained in the gap) will vary according to a variety of factors such as the thickness of a ionically conductive material (e.g., hydrogel patch) used with the electrode assembly, the diffusion characteristics of the chemical signal to be detected by the electrode subassembly for a given geometry, the size of the electrode subassembly, and the duration of the sensing period (i.e., monitoring period). For example, where the electrode assembly is used with an electrolytic hydrogel patch having a thickness in the range of about 10 $\mu$m to 1000 $\mu$m and the electrically insulating gap has a width in the range of about 10 $\mu$m to 1,000 $\mu$m. In a preferred embodiment, the ionically conductive material is from about 5 mil to 30 mil thick and the gap is about 5 mil wide.

The Working Electrode

The working electrode includes catalytic material on its catalytic surface, preferably Pt, PtO and/or $PtO_2$. The catalytic surface of the working electrode is the face of the electrode in contact with the electrolyte (e.g., a hydrogel patch) and which is responsible for conversion of chemical signal to electrical signal, and thus the face which constitutes the minimal portion of the electrode that must be composed of the catalytic material. The catalytic material of the catalytic surface is the material that promotes conversion of the chemical signal into an electrical signal. Exemplary catalytic materials include carbon as well as platinum, palladium, gold, iridium, or other nobel metal. Where the chemical signal to be detected is hydrogen peroxide (e.g., generated by catalysis of glucose by GOD), the preferred catalytic materials on the catalytic surfaces of the working electrodes are platinum, palladium, iridium, or other nobel metal, more preferably platinum or oxides, dioxides or alloys thereof.

The working electrode can be porous or nonporous, preferably nonporous. The working electrode can be made of catalytic material (e.g., stamped from a thin sheet of platinum). Although the electrode can be constructed from a single piece of material the working electrode must provide multiple substantially discontinuous working electrode surfaces to allow for multidirectional flow to the edges of the working electrode. The working electrode can be plated (e.g., electrolytic or nonelectrolytic plating), coated, printed, photolithographic ally deposited, or otherwise affixed to a substrate using methods well known in the art for application of a thin metal layer on a surface. The substrate can be composed of any insulating material (e.g., a ceramic, plastic (e.g., polyethylene, polypropylene), or polymeric material) to which the electrode assembly can be affixed. Preferably the electrode subassembly, more preferably the complete electrode assembly, is affixed to a plastic or ceramic substrate.

Preferably, the electrode subassembly and electrode assembly are manufactured in a manner that is the most economical without compromising electrode performance (e.g., the ability of the electrodes to catalyze the chemical signal, and/or conduct an electrical current, or the ability to manipulate the electrodes by hand without breaking or otherwise compromising the operability of the electrodes).

The working electrode can have the catalytic material over all electrode surfaces. Alternatively, only the catalytic faces of the electrode subassembly have the catalytic material. Preferably, the catalytic material is platinum or a platinum-containing material which is present on at least the catalytic surface of the working electrode.

The electrode assembly and/or electrode subassembly can include additional materials that enhance the performance, handleability, and/or durability of the electrode assembly and/or electrode subassembly. For example, the working electrode can be coated with a material that serves to decrease the interference of other species in the electrolyte with the measurement of electric current at the working electrode, and/or decrease the rate of oxidation of the catalytic material on the working electrodes' catalytic surfaces.

The relative size (i.e., diameter, surface area, thickness, etc.) of the working electrode and its individual components can vary according to a variety of factors, including the dimensions of the surface through which the chemical signal is to be detected (e.g., the size of a hydrogel patch through which the chemical signal is drawn), or the size constraints of a monitoring electrode assembly used in connection with the electrode subassembly. If desired, the working electrode including each of its components can be quite thin, with a thickness in the range of 0.25 $\mu$m to 250 $\mu$m.

Regardless of the embodiment used, all of the electrode subassemblies of the invention include (i) a working electrode comprised of a plurality of substantially discontinuous working electrode surfaces, allowing for measurement of multidirectional diffusion from a medium to the working electrode surfaces and (ii) an electrically insulating gap defined by the adjacent edges of the working electrode, which gap isolates the working electrode surfaces from each other. The relative proportions of each of the components (e.g., the width, surface areas, and geometries of the working electrode, and the width of the insulating gap) is such that substantially all chemical signal diffusing toward an outer edge of area defined by a working electrode surface allows for measurement of chemical diffused from multiple directions relative to a working electrode surface.

The electrode subassembly is normally used in an electrode assembly which includes additional components such as: a) an electroosmotic electrode (e.g., an iontophoresis or reverse iontophoresis electrode); b) a counter electrode; and c) a reference electrode. The electroosmotic electrode can be used electrically to draw electrochemical compounds from a source through material comprising water, enzyme and electrolyte, and to the area of the electrode subassembly. In general, practical and physical limitations of the system require that the electroosmotic electrode and the electrode subassembly be used alternately (i.e., current is present in the electroosmotic electrode or the electric current generated at the electrode subassembly is measured). Alternatively, diffusion of the chemical signal into the ionically conductive material can occur independent of the electroosmotic electrode (e.g., by passive diffusion).

The electrode assembly may comprise additional components. The electrode assembly may additionally comprise a chemical signal-impermeable mask which is positioned in the chemical signal transport path so as to inhibit substantially all chemical signal transport from the chemical signal source having an undesirable vector component relative to a plane of the mask and the catalytic faces of the working electrodes. Use of chemical signal-impermeable masks is not necessary to the operability of the invention and, in some cases, may not be desirable. Exemplary chemical signal-impermeable masks are disclosed within earlier filed application Ser. No. 08/527,061, filed Sep. 12, 1995, which application is incorporated herein by reference in its entirety and which application discloses inventions which were invented under an obligation to assign rights to the same entity as that to which the rights in the present invention were invented under an obligation to assign.

The electrode subassembly can be operated by connecting the electrodes such that the working electrode (including all of its components) are connected as two conventional working electrodes, along with appropriate counter and reference electrodes, to a standard potentiostat circuit(s). A potentiostat is an electrical circuit used in electrochemical measurements when a working electrode is biased at a potentials versus a reference electrode. For the purpose of the present invention, the electrical current measured at the working electrode of the electrode subassembly is the current that is correlated with an amount of chemical signal.

Figure 4:
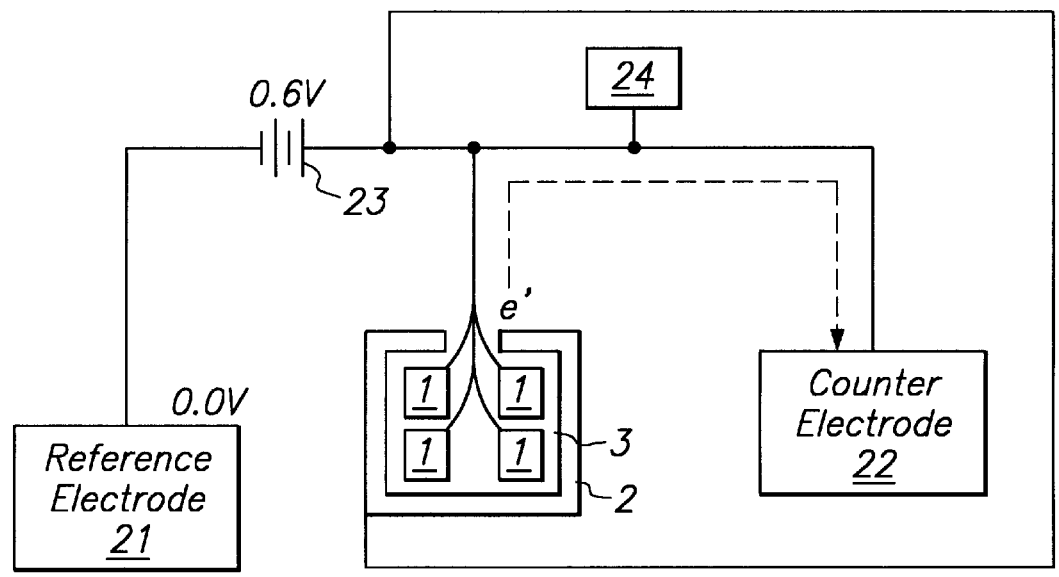
FIG. 4 is a schematic diagram of a device for measuring electrochemical signal which device uses the electrode subassembly and assembly of the invention.

FIG. 4 illustrates an example of an operating circuit using working electrode 1, reference electrode 21, and counter electrode 22 with a power source 23 and monitoring device 24. The power source 23 is used to provide voltage to the reference 21 and working 1 electrode to drive the conversion of chemical signal to electrical signal at the catalytic, multidimensional faces of the working 1 electrode. The power source 23 also maintains a fixed potential at the working electrode 1 (where, for example, hydrogen peroxide is converted to molecular oxygen, hydrogen ions, and electrons), which is compared with the potential of the reference electrode 21 during monitoring. The operating circuit also maintains an electrical potential on the working electrode 1 for catalysis of chemical signal that diffuses toward the working electrode 1. The working electrode 1 is electrically connected to a counter electrode 22. The counter electrode 22 consumes electrons generated at the working electrode. The current generated at the working electrode 1 is measured at a position between the working 1 and counter 22 electrode.

Based on the description above and in the figures, it will be recognized that the electrode subassembly and electrode assembly of the invention can be configured in a variety of different forms, and from a variety of different materials. However, the electrodes will have certain defined mechanical, electrical, chemical and diffusion characteristics.

Mechanically the electrode assembly and electrode subassembly will have sufficient structural integrity such that it can be readily handled by human fingers without significant handling difficulties or significantly compromising the performance of the electrode. Further, where the electrode subassembly is used in conjunction with an ionically conductive material (e.g., a hydrogel patch), it may be desirable to remove the material from the electrode. Thus, it may be desirable to design the electrode assembly so that the patch can be removed from the electrode assembly and/or electrode subassembly without significantly degrading the surface of any of the electrodes, or adhering to any of the electrodes in a manner that makes it difficult to remove completely all patch material from the face of any of the electrodes. The electrode subassembly and/or electrode assembly can be provided as a unit separate from the any other component of a monitoring device (e.g., a glucose monitoring device). In such an embodiment a bonding pad or a pad that contacts a pin connector member 4 as per FIGS. 1, 2 and 3 is used. The member 4 makes it possible readily to connect and disconnect the electrode assembly from the remainder of the device. Alternatively, the ionically conductive material and the electrode subassembly and/or electrode assembly can be provided as a single unit and the member 4 can be used electrically to connect the unit into the device and complete the device.

Preferably, the electrode assembly will optimally operate at a pH which is relatively close to that of the solid or electrolyte in which the electrode subassembly is in contact (e.g., human skin (about pH 7) or the hydrogel patch) and at least within a range of from about pH 4 to pH 9. In general, the working electrode operates at a current level in the range of 0.1 nanoamp to 1 milliamp.

Utility

The present invention is useful in connection with the detection of biologically significant molecules such as glucose which are moved through human skin using a technique known as electroosmosis. The basic concept of moving a molecule such as a glucose through human skin is disclosed within U.S. Pat. No. 5,362,307, issued Nov. 8, 1994, and U.S. Pat. No. 5,279,543, issued Jan. 18, 1994, which patents are incorporated herein by reference for disclosing the basic concept of moving molecules such as glucose through human skin by means of electroosmosis. The concept of converting the very small amounts of molecules such as glucose which can be extracted through the skin in order to create a current by use of glucose oxidase is disclosed within earlier filed application Ser. No. 08/265,084, filed Jun. 24, 1994, and application Ser. No. 08/373,931, filed Jan. 10, 1995; and hydrogel patches suitable for use with the present invention are disclosed within earlier filed application Ser. No. 08/501,664, filed Jul. 12, 1995, each of which applications are incorporated herein by reference in their entirety and which applications disclose inventions which were invented under an obligation to assign rights to the same entity as that to which the rights in the present invention were invented under an obligation to assign.

Figure 5:
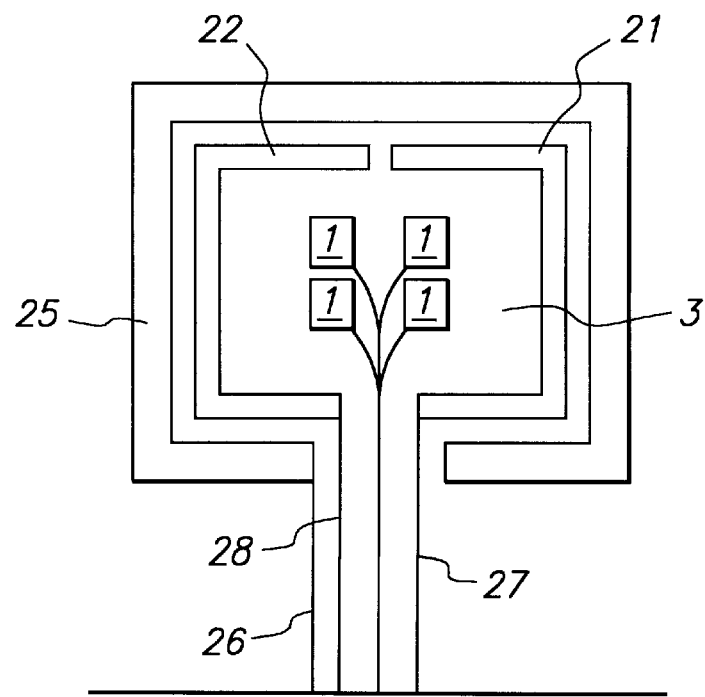
FIG. 5 is an overhead schematic view of one embodiment of an electrode assembly of the invention.

The electrode subassembly of the invention can be used as part of an electrode assembly (e.g., with reference, counter, and electroosmotic electrodes) for measurement of a biomedically important compound (e.g., glucose). For example, as shown in FIG. 5, the electrode subassembly comprised of a multicomponent working electrode 1 can be placed within a electroosmotic electrode 25, a reference electrode 21 and a counter electrode 22. The electroosmotic 25, reference 21 and counter 22 electrodes are connected by leads 26, 27 and 28, respectively, to a power source and monitoring device. A hydrogel patch, which is the electrochemical conducting medium, is placed in contact with the electrode assembly and the entire assembly placed onto an area of mammalian (e.g., human) skin. An electrical current is sent through the electroosmotic electrode, thereby drawing molecules, including glucose, through the patient's skin and into the hydrogel patch.

GENERATING ELECTRICAL SIGNAL

Figure 6:
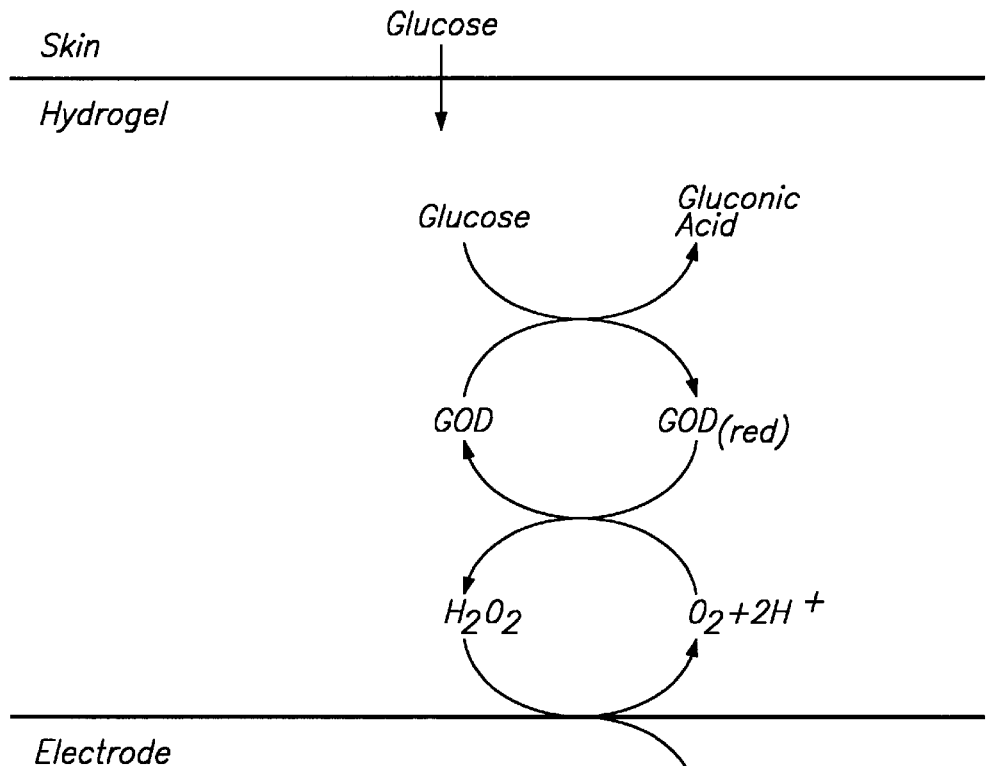
FIG. 6 is a schematic diagram of the chemical reactions involved in converting glucose to an electrical signal.

Glucose oxidase (GOD), contained in the hydrogel patch, catalyzes the conversion of glucose into gluconic acid and hydrogen peroxide as described above and shown in FIG. 6. The hydrogen peroxide is then catalyzed at the electrode subassembly to 2 electrons, molecular oxygen, and 2 hydrogen ions, and the electric current generated at the working electrode 1 measured relative to the reference electrode 21 as exemplified in FIG. 4. The electrical current generated at the working electrode 1 is correlated to the amount of glucose in the hydrogel patch, and extrapolated to the concentration of glucose in the subject's bloodstream.

The composition, size and thickness of the electrode assembly can be varied and such variance can affect the time over which the electrode assembly can be used. For example, the hydrogel patches and the electrodes of the present invention used with the electrode assembly are generally designed so as to provide utility over a period of about 24 hours. After that time some deterioration in characteristics, sensitivity, and accuracy of the measurements from the electrode can be expected (e.g., due to accumulation of material on the face of the electrode subassembly), and the electrode subassembly and hydrogel patch should be replaced. The invention contemplates electrode assemblies which are used over a shorter period of time, e.g., 8 to 12 hours or a longer period of time, e.g., 1 to 30 days.

The substantially discontinuous working electrode surfaces of the invention can be used to obtain improved signal to noise ratio and enhanced signal over an finite time when measuring any chemical signal in an finite volume. More specifically, the working electrode of the invention can be used to carry out a method which comprises extracting any biomedically significant substance through the skin of a mammalian subject (e.g., a human patient) and reacting that substance with another substance or substances to form a product which is detectable electrochemically by the production of a signal, which signal is generated proportionally based on the amount of a biologically important or biomedically significant substance drawn into the patch. As indicated in the above-cited patents the ability to withdraw biochemically significant substances such as glucose through skin has been established (see U.S. Pat. Nos. 5,362,307 and 5,279,543). However, the amount of compound withdrawn is often so small that it is not possible to make meaningful use of such methodology in that the withdrawn material cannot be precisely measured and related to any standard. The present invention provides an electrode that is capable of detecting the electrochemical signal at very low levels in a manner that allows for direct, accurate correlation between the amount of signal generated and the amount of the molecule in the human subject.

The invention is remarkable in that it allows for the noninvasive detection and quick, accurate measurement of amounts of a biomedically relevant compound, e.g., glucose, at levels that are 1, 2, or even 3 orders of magnitude less than the concentration of that compound in blood. For example, glucose might be present in blood in a concentration of about 5 millimolar. However, the concentration of glucose in a hydrogel patch which is used to withdraw glucose through skin as described in the system above is on the order of 2 micromolar to 100 micromolar. Micromolar amounts are 3 orders of magnitude less than millimolar amounts. The ability accurately and quickly to detect glucose in such small concentrations is attained by constructing the electrode assembly and electrode subassembly with the components described herein and the configurations described herein.

Because the amount of signal to be measured may be very small and further because it may be important to measure changes quickly in that signal over short periods of time the multicomponent, multisurface electrode configuration of the invention is valuable in obtaining results. The electrodes of the invention can detect a smaller signal over a shorter period of time as compared to a continuous surface working electrode.

EXAMPLES

The following examples are put forth so as to provide those of ordinary skill in the art with a complete disclosure and description of how to use the electrode assemblies and subassemblies of the present invention, and are not intended to limit the scope of what the inventors regard as their invention. Efforts have been made to ensure accuracy with respect to numbers used (e.g., amounts, particular components, etc.), but some deviations should be accounted for. Unless indicated otherwise, parts are parts by weight, surface area is geometric surface area, temperature is in degrees centigrade, and pressure is at or near atmospheric pressure.

Figure 10:
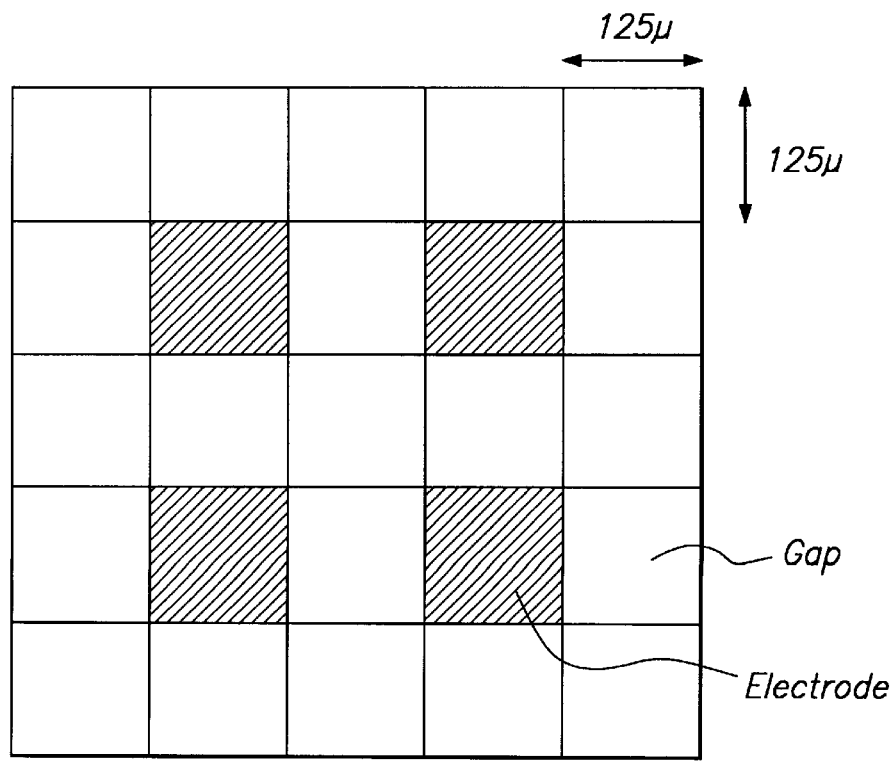
FIG. 10 is an overhead view of a simple "checkerboard" embodiment of a working electrode of the invention.
Figure 12:
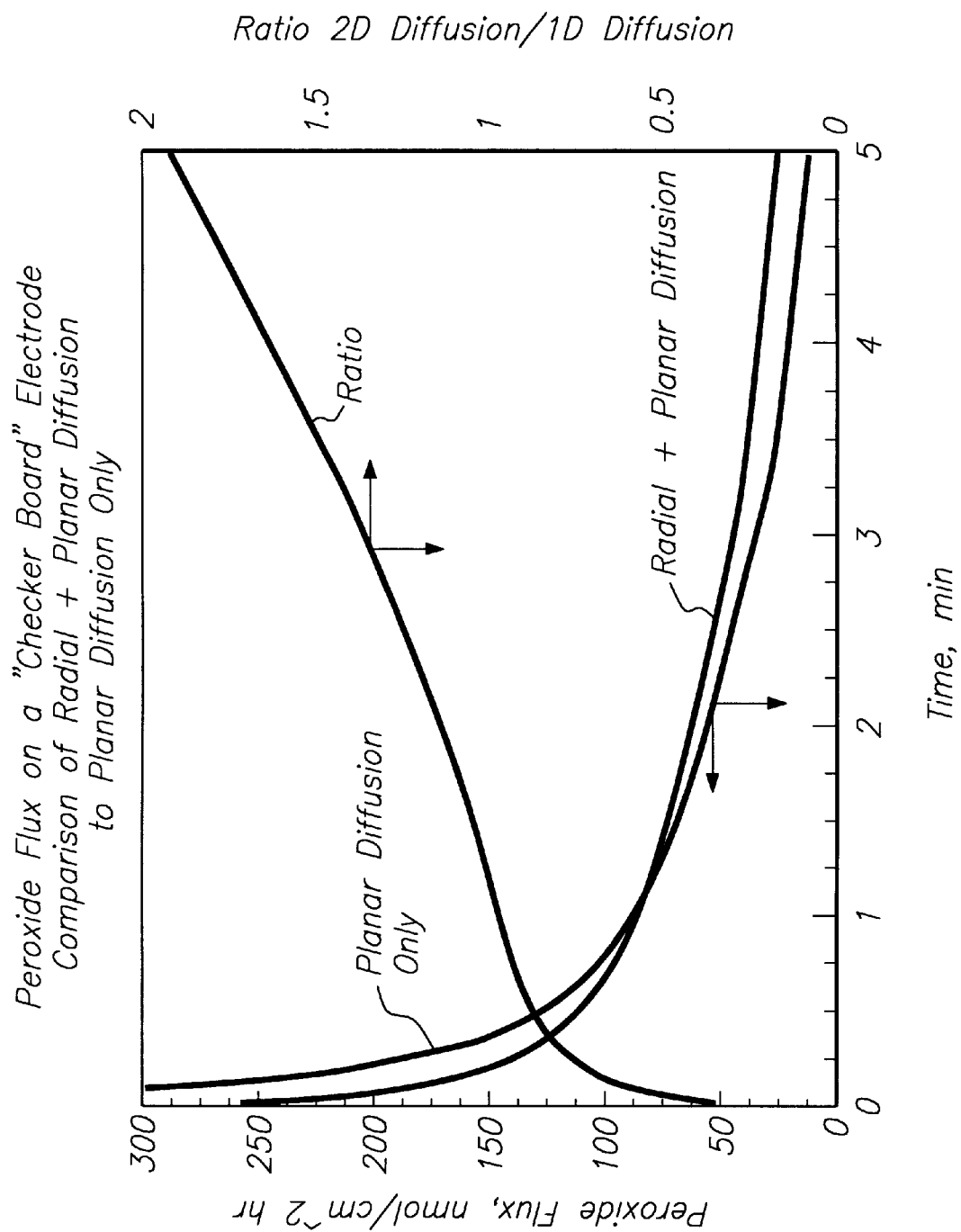
FIG. 12 is a graph comparing flux for an embodiment as per FIG. 10 with a single planar continuous working electrode surface.
Figure 13:
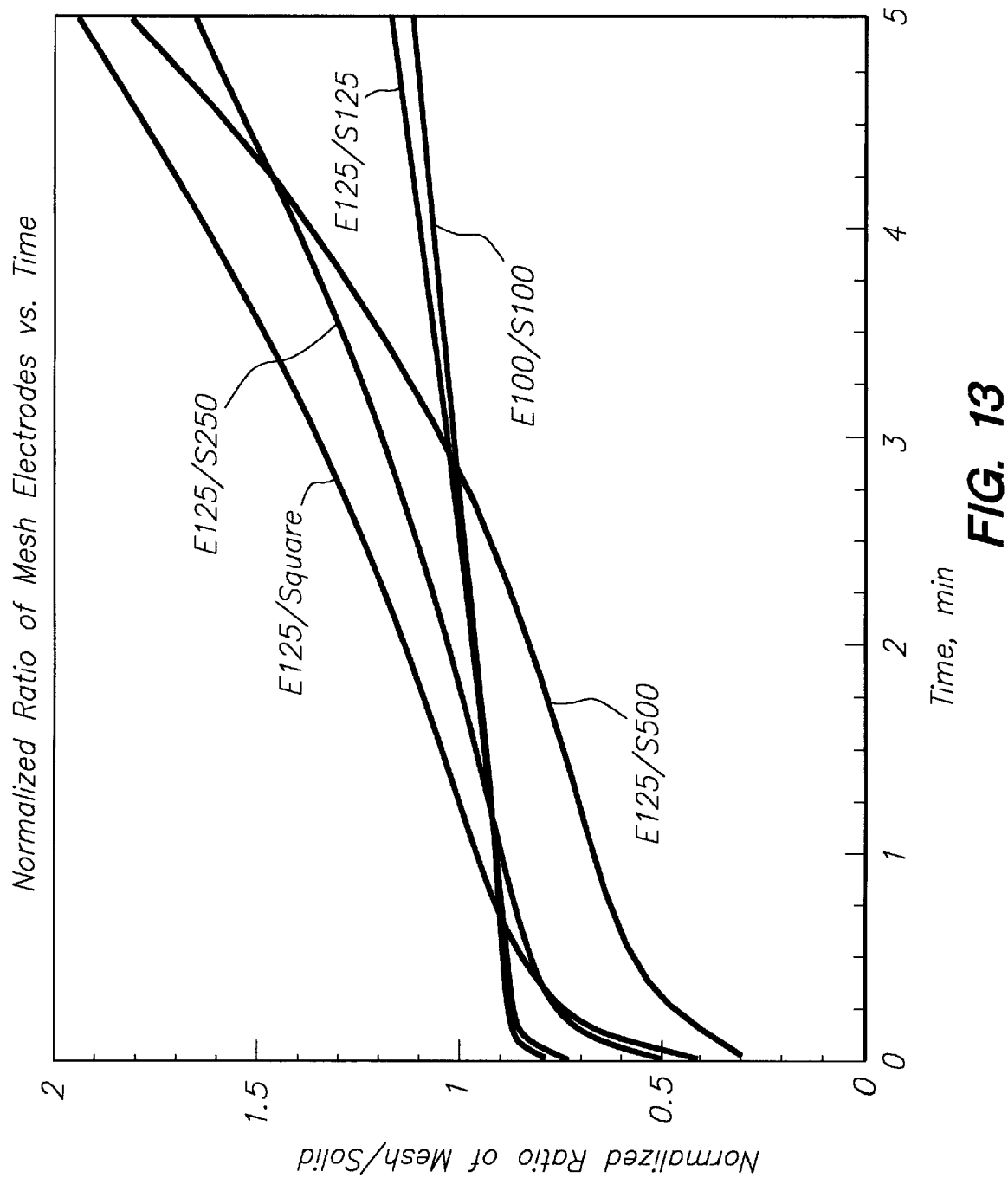
FIG. 13 is a graph comparing various dimensional changes in "strip" and "checkerboard" electrodes relative to a with a single planar continuous working electrode surface.

The data presented in these examples are computer-simulated (i.e., the data is generated from a computer model of the electrode assembly described herein). The computer model of the invention uses the following parameters:

peroxide diffusivity: $1.2 \times 10^{-5}$ cm$^2$/sec;

glucose diffusivity: $1.3 \times 10^{-6}$ cm$^2$/sec;

initial peroxide concentration=100 nmol/ml=100 $\mu$M;

thickness of stagnant layer on top of electrode (the gel layer)=600 microns;

electrode thickness=125 micron width for the strip configuration as per FIG. 7 and 125 micron squares for the checkerboard configuration as per FIG. 10;

gap (insulator)=125 microns, 250 microns and 500 microns for the strip configuration, as indicated in FIGS. 11, 12, and 13.

Example 1

Effect of Edges and Radial Diffusion on Peroxide Flux at an Electrode Surface

FIG. 11 provides a computer simulation of the effect of edges and radial diffusion on peroxide flux at an electrode surface. This simulation shows that the peroxide flux on a slotted discontinuous electrode is higher at all positions, and particularly so at and near the edges, as compared to the peroxide flux for a planar electrode.

Example 2

Peroxide Flux on a Checker Board Electrode

FIG. 12 provides a computer simulation of peroxide flux on a "checker board" electrode; radial and planar diffusion are compared with radial diffusion only. This simulation shows the peroxide flux on a checkerboard relative to the peroxide flux on a planar electrode (with ID diffusion only). The curves are normalized for the same surface area of the electrode. Also shown is the ratio of the flux for checkerboard divided by the flux for the planar electrode. This ratio curve clearly shows that there is a significant advantage in using a discontinuous surface (such as a checkerboard) as compared to a planar electrode.

Example 3

Comparison of Checker Board, Slotted, and Solid Electrodes

FIG. 13 is a graph of a computer simulation of results comparing a normalized ratio of mesh to solid electrodes over time. This simulation shows the peroxide flux for slotted and square electrodes (E) with spacing (S) relative (normalized) to the peroxide flux for a 1D planar electrode. In all cases, the results are normalized so that the electrodes have the same surface area. The conclusion from this graph is that the checkerboard (square) electrode is best, followed by the 125 micron/250 micron space slotted electrode, and so on for the remaining electrodes.

We claim:

1. A method of measuring the amount or concentration of a chemical signal in a mammalian subject, the method comprising the steps of:

contacting the skin of the mammalian subject with a first surface of a hydrogel medium through which a chemical signal can diffuse in response to a current, said hydrogel comprising water, electrolyte, and an enzyme, wherein the thickness of said hydrogel is in the range of 10 $\mu$m to 1,000 $\mu$m;

contacting an electrode assembly to a second surface of the medium, the assembly comprising a working electrode comprised of a plurality of substantially physically separated electrode surfaces and an electroosmotic electrode, wherein (i) the working electrode surfaces are separated by a gap having a width in a range of 10 $\mu$m to 1,000 $\mu$m, (ii) an electrically insulating material is positioned in each gap separating the electrode surfaces, (iii) the working electrode is characterized by a substantially planar configuration, and (iv) the working electrode has a thickness in a range of 0.25 $\mu$m to 250 $\mu$m;

providing current to the electroosmotic electrode sufficient to create diffusion of a chemical signal across the mammalian subject's skin, through the medium and to the working electrode in a first dimension direction and a second dimension direction;

providing a voltage to each of the working electrode surfaces of the working electrode sufficient to drive electrochemical detection of chemical signal which generates an electrical current at the working electrode surfaces, wherein said electrical current is generated at the working electrode surfaces by electrochemical oxidation of hydrogen peroxide producing an electrical signal;

measuring the electrical current generated at the working electrode surfaces; and correlating the measured current to the amount or concentration of chemical signal in the mammalian subject.

2. The method of claim 1, wherein the electrode surfaces are configured as elongated rectangular strips parallel to each other and separated from each other by elongated rectangular gaps.

3. The method of claim 1, wherein diffusion of chemical signal further occurs in a third dimension direction substantially normal to the second dimension direction.

4. The method of claim 3, wherein the electrode surfaces are configured in a regular pattern of planar surfaces and gaps.

5. The method of claim 1, wherein each working electrode surface is comprised of a compound selected from the group consisting of platinum, platinum alloy, oxides and dioxides thereof.

6. The method of claim 1, wherein the electrode assembly further comprises a counter electrode and a reference electrode and wherein the counter electrode and a reference electrode are positioned in substantially the same plane as the working electrode, the counter electrode being electrically connected to the working electrode, and the reference electrode being positioned such that a substantially constant electrical potential is maintained on the reference electrode relative to the working electrode.

7. The method of claim 6, wherein the working electrode, counter electrode, reference electrode, and electroosmotic electrode are concentrically aligned with each other and wherein the working electrode is operated at a current level in the range of 0.1 nanoamp to 1 milliamp.

8. The method of claim 6, wherein the medium comprises a hydrogel having a surface in contact with a surface of the working electrode, the counter electrode, the reference electrode, and the electroosmotic electrode.

9. The method of claim 1, wherein the chemical signal is glucose.

10. The method of claim 1, wherein the working electrode surfaces are provided as a plurality of square-shaped regions, with the working electrode surfaces being isolated from each other by a plurality of rectangular gaps.

11. The method of claim 10, wherein the rectangular gaps are squares.

12. A method of measuring the amount or concentration of glucose in a human patient, comprising the steps of:

contacting the skin of the patient with a first surface of a hydrogel medium through which glucose diffuses, said hydrogel comprising water, electrolyte and glucose oxidase, wherein (i) glucose oxidase catalyzes a reaction resulting in conversion of glucose to gluconic acid, (ii) the thickness of said hydrogel is in the range of 10 $\mu$m to 1,000 $\mu$m;

contacting an electrode assembly to a second surface of the hydrogel medium, the assembly comprising a working electrode comprised of a plurality of substantially physically separated working electrode planar surfaces and an electroosmotic electrode, wherein (i) the working electrode surfaces are separated by a gap having a width in a range of 10 $\mu$m to 1,000 $\mu$m, (ii) an electrically insulating material is positioned in each gap separating the electrode surfaces, (iii) the working electrode is characterized by a substantially planar configuration, and (iv) the working electrode has a thickness in a range of 0.25 $\mu$m to 250 $\mu$m;

providing current to the electroosmotic electrode sufficient to draw ions through the skin of the patient along with glucose wherein the working electrode planar surfaces are configured such that the glucose is drawn in a first direction normal to the planar surfaces and in a second direction substantially parallel to the planar surfaces;

providing a voltage to each of the working electrode surfaces sufficient to drive electrochemical detection of a product of the reaction of glucose and glucose oxidase which generates an electrical current at the working electrode surfaces;

measuring the electrical current at the working electrode surfaces; and correlating the measured current to the amount or concentration of glucose in the patient.

13. The method of claim 12 wherein the working electrodes are configured such that the glucose is further drawn in a third direction substantially parallel to the planar surfaces and substantially perpendicular to the second direction.

14. A hydrogel and electrode assembly for use in a glucose monitoring device, comprising:

a hydrogel comprised of water, electrolyte and glucose oxidase, wherein (a) glucose oxidase catalyzes a reaction resulting in conversion of glucose to gluconic acid, and (b) the thickness of said hydrogel is in the range of 10 $\mu$m to 1,000 $\mu$m; and an electrode assembly comprising a working electrode that comprises a plurality of substantially physically separated working electrode planar surfaces, wherein (i) each working electrode surface comprises a catalytic surface and is separated from adjacent working electrode surfaces by a gap, said gap having a width in a range of 10 μm to 1,000 μm, (ii) an electrically insulating material is positioned in each gap separating the electrode surfaces, (iii) the working electrode is characterized by a substantially planar configuration, (iv) the working electrode has a thickness in a range of 0.25 μm to 250 μm, and v) a voltage may be provided to each of the working electrode surfaces sufficient to drive electrochemical detection of a product of the reaction of glucose and glucose oxidase which generates an electrical current at the working electrode surfaces.

15. The hydrogel and electrode assembly of claim 14, which further comprises a counter electrode and a reference electrode, each being positioned in substantially the same plane as the working electrode, the counter electrode being electrically connected to the working electrode, and the reference electrode being positioned such that a substantially constant electrical potential is maintained on the reference electrode relative to the working electrode.

16. The hydrogel and electrode assembly of claim 15, wherein the working electrode surfaces are provided as a plurality of square-shaped regions, with the working electrode surfaces being isolated from each other by a plurality of rectangular gaps.

17. The hydrogel and electrode assembly of claim 16, wherein the rectangular gaps are squares.

18. The hydrogel and electrode assembly of claim 14, wherein the electrode surfaces are configured as elongated rectangular strips parallel to each other and separated from each other by elongated rectangular gaps.

19. The hydrogel and electrode assembly of claim 14, wherein each working electrode surface is comprised of a compound selected from the group consisting of platinum, platinum alloy, oxides and dioxides thereof.

20. The hydrogel and electrode assembly of claim 14, wherein the electrode assembly further comprises an electroosmotic electrode, a counter electrode and a reference electrode and wherein the electroosmotic electrode, the counter electrode and a reference electrode are positioned in substantially the same plane as the working electrode, the counter electrode being electrically connected to the working electrode, and the reference electrode being positioned such that a substantially constant electrical potential is maintained on the reference electrode relative to the working electrode.

21. The hydrogel and electrode assembly of claim 20, wherein the working electrode, counter electrode, reference electrode, and the electroosmotic electrode are concentrically aligned with each other and wherein the working electrode is operated at a current level in the range of 0.1 nanoamp to 1 milliamp.

22. The hydrogel and electrode assembly of claim 20, wherein the hydrogel has a surface in contact with a surface on the working electrode, the counter electrode, the reference electrode, and the electroosmotic electrode.

23. A method of measuring the amount or concentration of a chemical signal in a mammalian subject, the method comprising the steps of:
contacting a first surface of an ionically conductive hydrogel with a skin surface of the mammalian subject, said hydrogel comprising water, electrolyte, and an enzyme, wherein the thickness of said hydrogel is in the range of 10 μm to 1,000 μm;
contacting an electrode assembly to a second surface of the hydrogel, the assembly comprising an electroosmotic electrode, a working electrode comprised of a plurality of substantially physically separated working electrode planar surfaces, a counter electrode, and a reference electrode, wherein (i) the working electrode surfaces are separated by a gap having a width in a range of 10 μm to 1,000 μm, (ii) an electrically insulating material is positioned in each gap separating the electrode surfaces, (iii) the working electrode is characterized by a substantially planar configuration, and (iv) the working electrode has a thickness in a range of 0.25 μm to 250 μm;
providing current to the electroosmotic electrode sufficient to draw the chemical signal across the mammalian subject's skin, through the hydrogel and to the working electrode;
providing a voltage to the working electrode planar surfaces sufficient to drive electrochemical detection of chemical signal which generates an electrical current at the working electrode surfaces, wherein said electrical current is generated at the working electrode surfaces by electrochemical oxidation of hydrogen peroxide producing an electrical signal;
measuring the electrical current generated at the working electrode; and
correlating the measured current to the amount or concentration of chemical signal in the mammalian subject.

24. A method of measuring the amount or concentration of glucose in a mammalian subject, the method comprising the steps of:
contacting a first surface of an ionically conductive hydrogel with a skin surface of the mammalian subject, said hydrogel comprising water, electrolyte and glucose oxidase, wherein (i) glucose oxidase catalyzes a reaction resulting in conversion of glucose to gluconic acid, and (ii) the thickness of said hydrogel is in the range of 10 μm to 1,000 μm;
contacting an electrode assembly to a second surface of the hydrogel, the assembly comprising an electroosmotic electrode, a working electrode comprised of a plurality of substantially physically separated working electrode planar surfaces, a counter electrode, and a reference electrode, wherein (i) the working electrode surfaces are separated by a gap having a width in a range of 10 μm to 1,000 μm, (ii) an electrically insulating material is positioned in each gap separating the electrode surfaces, (iii) the working electrode is characterized by a substantially planar configuration, and (iv) the working electrode has a thickness in a range of 0.25 μm to 250 μm;
providing current to the electroosmotic electrode sufficient to draw the glucose across the mammalian subject's skin and into the hydrogel;
providing a voltage to the working electrode planar surfaces sufficient to drive electrochemical detection of a product of the reaction of glucose and glucose oxidase which generates an electrical current at the working electrode surfaces;
measuring the electrical current generated at the working electrode; and
correlating the measured current to the amount or concentration of glucose in the mammalian subject.

* * * * *